United States Patent [19]

Thomas

[11] Patent Number: 4,955,871
[45] Date of Patent: * Sep. 11, 1990

[54] SINGLE-USE DISPOSABLE SYRINGE

[75] Inventor: Ronny D. Thomas, Bellevue, Wash.

[73] Assignee: PATH, Seattle, Wash.

[ * ] Notice: The portion of the term of this patent subsequent to Nov. 28, 2006 has been disclaimed.

[21] Appl. No.: 360,125

[22] Filed: Jun. 1, 1989

Related U.S. Application Data

[63] Continuation-in-part of Ser. No. 44,054, Apr. 29, 1987, abandoned, and a continuation-in-part of Ser. No. 199,612, May 27, 1988, Pat. No. 4,883,473.

[51] Int. Cl.$^5$ .......................... A61M 5/18; A61M 5/32
[52] U.S. Cl. .................... 604/217; 604/132; 604/204; 222/95; 222/107; 222/215
[58] Field of Search ............... 604/204, 132, 198, 110, 604/411, 413, 217; 222/92, 95, 107, 206, 215

[56] References Cited

U.S. PATENT DOCUMENTS

| | | |
|---|---|---|
| 1,021,146 | 3/1912 | Greeley . |
| 1,687,502 | 10/1928 | Marcy . |
| 1,948,306 | 2/1934 | Meurer .......................... 604/204 X |
| 2,371,086 | 3/1945 | Watson et al. . |
| 2,618,263 | 11/1952 | Lakso et al. . |
| 2,625,157 | 1/1953 | Lockhart . |
| 2,642,064 | 6/1953 | Lawshe . |
| 2,667,872 | 2/1954 | Smith .......................... 604/204 X |
| 2,677,373 | 5/1954 | Barradas . |
| 2,680,440 | 6/1954 | Fox . |
| 2,693,183 | 11/1954 | Lockhart . |
| 2,757,671 | 8/1956 | Haafkens . |
| 2,764,979 | 10/1956 | Henderson . |
| 3,128,920 | 4/1964 | Volckening et al. ............ 222/215 |
| 3,252,625 | 5/1966 | Cattaneo .................... 222/215 X |
| 3,335,914 | 8/1967 | Strazdins et al. .................... 222/107 |
| 3,496,937 | 2/1970 | Balson .............................. 604/132 |
| 3,512,524 | 5/1970 | Drewe ........................... 604/204 X |
| 3,552,604 | 1/1971 | Gordon .............................. 222/215 |
| 3,736,933 | 6/1973 | Szabo . |
| 3,773,047 | 11/1973 | Sneider . |
| 4,013,073 | 3/1977 | Cunningham . |
| 4,018,222 | 4/1977 | McAleer et al. ............... 604/204 X |
| 4,022,206 | 5/1977 | Hilleman et al. .................. 206/365 |
| 4,130,117 | 12/1978 | Van Eck . |
| 4,261,482 | 4/1981 | Yamada et al. ..................... 222/215 |
| 4,282,986 | 8/1981 | af Ekenstam et al. .................. 222/1 |
| 4,391,273 | 7/1983 | Chiquiar-Arias ................... 604/110 |
| 4,475,906 | 10/1984 | Holzner .............................. 604/212 |
| 4,548,601 | 10/1985 | Lary .................................... 604/204 |
| 4,573,977 | 3/1986 | Crawford ........................... 604/212 |
| 4,758,230 | 7/1988 | Rycroft .............................. 222/604 |
| 4,883,473 | 11/1989 | Thomas .............................. 604/217 |

FOREIGN PATENT DOCUMENTS

1478143 4/1967 France ................................ 604/204

Primary Examiner—C. Fred Rosenbaum
Assistant Examiner—Sharon Rose
Attorney, Agent, or Firm—Finnegan, Henderson, Farabow, Garrett & Dunner

[57] ABSTRACT

A single-use disposable syringe. In the syringe, a reservoir is formed of two sheets of thermoplastic material having expanded central portions that form a pair of convex domes. Both of the domes are compressible, and a connecting member spaces apart the domes. In response to complete compression of both of the central portions together, the reservoir substantially collapses and each of the domes becomes concave to prevent the reservoir from being reformed and to prevent reuse of the syringe. After partial compression of both of the central portions together and partial collapse of the reservoir, the central portions expand to reform the reservoir and draw fluid into the reservoir, thereby aspirating a hypodermic needle.

24 Claims, 2 Drawing Sheets

SINGLE-USE DISPOSABLE SYRINGE

FEDERALLY-SPONSORED RESEARCH AND DEVELOPMENT

The U.S. Government has contributed support to this invention under Federal Grant Number DPE-5968-A-00-7035-00 awarded by the Agency for International Development. The U.S. Government has certain rights in the invention.

CROSS-REFERENCES TO RELATED APPLICATIONS

This application is a continuation-in-part of application Ser. No. 07/044,054, filed Apr. 29, 1987, now abandoned, entitled Single Use Injection Device. This application also is a continuation-in-part of application Ser. No. 07/199,612, filed May 27, 1988, now U.S. Pat. No. 4,883,473, entitled Single Use Injection Device.

FIELD OF THE INVENTION

This invention relates to the structure and manufacture of syringes, and more particularly to syringes that cannot be reused.

BACKGROUND OF THE INVENTION

The rapid spread of acquired immune deficiency syndrome (AIDS) among intravenous drug users has created an urgent need for syringes that cannot be reused. In many situations, injections are given to patients without carefully controlling access to syringes. The use of reusable syringes under those circumstances increases the risk of infection. An infection can occur whenever syringes that have been used previously, and which therefore are no longer sterile, are used to administer injections.

Of course, reusable syringes are suitable for administration of a vaccine or other injectable medicaments when the injections are performed by a professional staff in formal health care facilities. In a hospital environment, skilled personnel sterilize the syringe for reuse, refill the syringe with the appropriate medicament, and personally administer the injections. Furthermore, circulation of these syringes is managed and controlled.

However, there are times when it is necessary or more economical to administer injections outside a hospital environment. For example, it may be necessary to give injections to a large number of individuals over a short period of time, patients may be located in a developing country or in an area without convenient access to a hospital or medical personnel, or it may be desirable to permit injections to be administered to a patient at his or her home or while he or she travels. Under these circumstances, it is virtually impossible to prevent misuse of the syringes. Furthermore, it is much more difficult to ensure proper sterilization of the syringes, particularly if medicaments are administered by non-professional personnel.

It is also important to develop an easy method of manufacturing a syringe that cannot be reused. Even though the use of disposable syringes reduces the risk of infection, it is not economically feasible to replace reusable syringes with disposable syringes unless the disposable syringes are made in a relatively inexpensive manner. Unfortunately, single use syringes that have been developed often are expensive to manufacture, or are so bulky that the syringes are inconvenient to ship and store.

In order to ensure proper administration of an injection, it is important that the syringe be designed to allow aspiration to verify proper placement of the needle in the patient. Trained medical personnel confirm whether a needle is or is not in a blood vessel by aspirating prior to injection of a medicament. In aspiration, a negative or suction pressure causes the needle to draw material into the syringe from the patient. The person administering the injection then visually examines the syringe to see if any blood has been drawn into the syringe through the needle. If, for example, the injection should be administered intravenously, the presence of blood after aspiration indicates proper placement of the needle.

The goals of designing a syringe that can be aspirated and which cannot be reused appear to be in conflict. Disposable syringes that contain a prefilled vaccine delivery system typically have a squeezable body portion or other elastic receptacle. In these syringes, a positive pressure is applied on or by the receptacle to force the medicament out through the needle. In order to perform aspiration, however, a negative pressure is applied to the receptacle. Unfortunately, the negative pressure needed to aspirate the syringe also may be used to reform the elastic receptacle, allowing the syringe to be reused.

Therefore, there is a need for an inexpensive and easy to manufacture syringe that cannot be reused, but which can be used to perform aspiration.

SUMMARY OF THE INVENTION

It is an object of the present invention to avoid some of the problems and disadvantages associated with prior art syringes.

It is therefore desirable to provide an injection device which cannot be reused.

There is great concern among public health officials about reducing the possibility of transmission of blood borne diseases by the use or reuse of an improperly sterilized or unsterilized needle and syringe. In some U.S. cities the spread of AIDS is growing most rapidly due to the sharing of needles and syringes by intravenous drug abusers. In addition, many third world countries reuse disposable syringes, with the potential of spreading blood borne diseases. An invention that renders a disposable syringe nonreusable may have an important impact on reducing any potential risks. There is the potential for rapid application and use of such an invention in containing the national and international spread of AIDS and other blood borne diseases.

It also would be beneficial to provide a disposable injection device which is easily used in the field by non-professional but trained personnel. Preferably, the injection device would be rendered incapable of reuse by providing a reservoir that collapses when emptied of contents during administration of an injection. Additionally, the reservoir for the injection device should have sufficient elasticity and integrity to permit aspiration during the early stages of administration of the injection.

Finally, it would be advantageous to provide an injection device that can be economically manufactured using a fabrication process which incorporates steps that create a reservoir that is sealed properly but which is structured to collapse when the reservoir is emptied a single time.

To achieve the objects and in accordance with the purpose of the invention, as embodied and broadly described herein, the single-use disposable syringe of this invention includes needle assembly means for injecting the medicament into the patient. The syringe also is provided with reservoir means for storing the medicament and for expelling the medicament into the needle assembly means. The reservoir means includes two sheets of thermoplastic material, wherein each of the two thermoplastic sheets is comprised of an expanded central portion, an expanded injection neck portion, an expanded filling neck portion, and a substantially flat peripheral portion. The substantially flat peripheral portions of the two sheets of thermoplastic material are opposite and coextensive to each other and are sealed together face-to-face, and the expanded central portions are opposite and coextensive to each other, to form a reservoir for storing the medicament. The expanded injection neck portions extend from the expanded central portions to a first end of each sheet, and are opposite and coextensive to each other, to form an injection port extending from the reservoir and connected to the needle assembly means for directing the medicament from the reservoir to the needle assembly means. The expanded filling neck portions extend from the expanded central portions to a second end of each sheet, and are opposite and coextensive to each other, to form a filling port extending from the reservoir for filling the reservoir with the medicament. The expanded central portions are compressible, and in response to complete compression of both of the central portions together, the reservoir substantially collapses to prevent the reservoir from being reformed and to expel the medicament out of the reservoir. In response to partial compression of both of the central portions together, the reservoir partially collapses to expel some of the medicament out of the reservoir. The central portions, after partial compression of both of the central portions together and partial collapse of the reservoir, expand to reform the reservoir and to draw fluid into the reservoir, thereby aspirating the needle assembly means.

In one embodiment of the single-use disposable syringe of the invention, the substantially flat peripheral portions of the two sheets of thermoplastic material are sealed together face-to-face prior to formation of the expanded portions of the two sheets. The central portions of the two sheets, and the injection neck portions and filling neck portions extending therefrom, are expanded to form the reservoir, injection port, and filling port after the peripheral portions are sealed together, by injecting compressed gas between the appropriate portions of the two sheets or by drawing apart the appropriate portions of the two sheets using a vacuum, until those portions expand to fill a cavity of a mold.

In another embodiment of the single-use disposable syringe, the expanded central portions form a reservoir that comprises a compressible convex first dome, a compressible convex second dome, and a connecting member. The connecting member, which is coupled to the first and second domes, is provided for spacing apart the first and second domes, and for enabling the reservoir to substantially collapse in response to complete compression of both of the domes together. In response to complete compression of both of the domes together, each of the domes becomes concave to prevent the reservoir from being reformed.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

The accompanying drawings, which are incorporated in and constitute a part of this specification, illustrate an embodiment of the invention, and together with the description, serve to explain the principles of the invention.

DESCRIPTION OF THE PREFERRED EMBODIMENTS

Reference will now be made in detail to the present preferred embodiments of the invention, examples of which are illustrated in the accompanying drawings.

Figure 1:
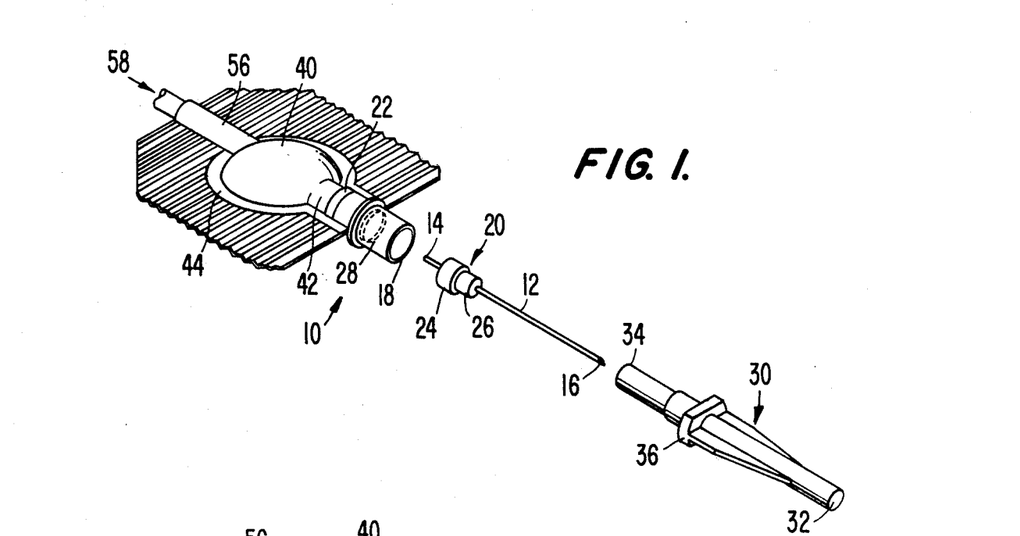
FIG. 1 is diagram of embodiment of the present invention showing a needle assembly means in greater detail.

An embodiment of a single-use disposable syringe for providing a medicament for injection into a patient is shown in FIG. 1 and is represented graphically by the numeral 10.

In accordance with the invention, the syringe includes needle assembly means for injecting the medicament into the patient. The needle assembly means includes a hypodermic needle. As embodied in syringe 10 shown in FIG. 1, a hypodermic needle 12 is provided that is pointed at both ends 14 and 16.

The needle assembly means contains hub means fastened to the hypodermic needle for supporting the hypodermic needle, and a tube for holding the hypodermic needle and the hub means, having a closed end connected to an injection port and an open end. Preferably, the tube is provided by a nozzle 18, the hub means is provided by a needle hub 20, and the closed end of the tube is formed by a nozzle membrane 22.

Figure 2:
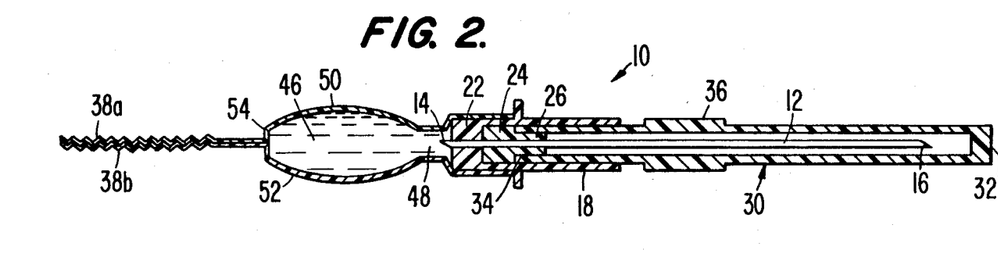
FIG. 2 is a diagram of an embodiment of the present invention after piercing of a membrane with a needle.

As illustrated in FIGS. 1 and 2, hypodermic needle 12 passes through needle hub 20. The needle hub is made of polystyrene and is secured to hypodermic needle 12 using epoxy resin as an adhesive. In this embodiment, nozzle 18 and needle hub 20 are cylindrical in shape. Preferably, needle hub 20 is comprised of a first section 24 of large diameter and a second section 26 of small diameter. The dimensions of large diameter first section 24 and of the internal diameter of nozzle 18 are selected so that needle hub 20 is frictionally held within nozzle 18, but can be moved laterally within nozzle 18 when a force is applied to needle hub 20. One of the sharp pointed ends 14 of hypodermic needle 12 penetrates nozzle membrane 22 when needle hub 20 is moved toward the nozzle membrane. The other sharp pointed end 16 of hypodermic needle 12 is used to pierce the skin of the patient so that the medicament can be administered intravenously or intramuscularly.

As embodied herein, nozzle 18 also is provided with an internal rib 28 between nozzle membrane 22 and needle hub 20 to prevent pointed end 14 of the hypodermic needle from piercing the closed end of the tube unless a sufficient force is applied. The dimensions of large diameter first section 24 and of internal rib 28 are selected so that needle hub 20 will not move past rib 28 unless a relatively larger force is applied to needle hub 20. This structure reduces the risk of unintentional piercing of nozzle membrane 22 at times when no one is ready to administer an injection.

Means are provided for protecting the hypodermic needle. As shown in FIG. 1, syringe 10 has a protector cap 30. Protector cap 30 is a cylinder having a closed end 32 and an open end 34. Protector cap 30 is long enough, together with nozzle 18, to enclose hypodermic needle 12 without permitting the closed end of the protector cap to come into contact with sharp pointed end 16 of the hypodermic needle. The open end of the protector cap fits inside the nozzle, and preferably the external diameter of the open end is selected so that the protector cap is snugly held in position within nozzle 18. As a result, the hypodermic needle is kept sterile and is not exposed during storage and shipment of the syringe. Following the piercing of nozzle membrane 22, protector cap 30 is removed in order to administer an injection. After the syringe has been used to inject a medicament into a patient, the protector cap can be reinserted into nozzle 18 and used as a protective cover over the hypodermic needle to prevent accidental stabbing by sharp pointed end 16. As embodied herein, the protector cap is made of polyethylene.

The means for laterally moving the hypodermic needle within the tube to pierce the closed end of the tube with one of the pointed ends of the hypodermic needle is provided by cooperation of protector cap 30 with needle hub 20. The internal diameter of open end 34 of the protector cap is selected so that the small diameter second section 26 of needle hub 20 fits snugly within the open end of the protector cap. The external diameter of open end 34 of the protector cap is selected so that the protector cap can be moved laterally within nozzle 18. This design permits lateral movement of hypodermic needle 12 without angular displacement of the needle as it moves toward and through nozzle membrane 22 at the closed end of nozzle 18.

As shown in FIG. 2, protector cap 30 can be used as a tool, in which open end 34 of the protector cap is pushed against the large diameter first section 24 of needle hub 20. In this way, a sufficient force can be safely applied to needle hub 20 to force it past internal rib 28. Protector cap 30 then continues pushing large diameter first section 24 of needle hub 20 until sharp pointed end 14 of hypodermic needle 12 penetrates nozzle membrane 22. The protector cap is long enough to allow needle hub 20 and hypodermic needle 12 to be laterally moved far enough within nozzle 18 to pierce nozzle membrane 22 with sharp pointed end 14 of the hypodermic needle.

As embodied herein, protector cap 30 also may be provided with an external rim 36. External rim 36 allows a person handling the syringe to more easily control the lateral movement of needle hub 20 within the nozzle by applying a force to the external rim.

In accordance with the invention, the syringe includes reservoir means for storing the medicament and for expelling the medicament into the needle assembly means. The reservoir means includes two sheets of thermoplastic material. Each of the two thermoplastic sheets has an expanded central portion, an expanded injection neck portion, and a substantially flat peripheral portion.

Figure 3:
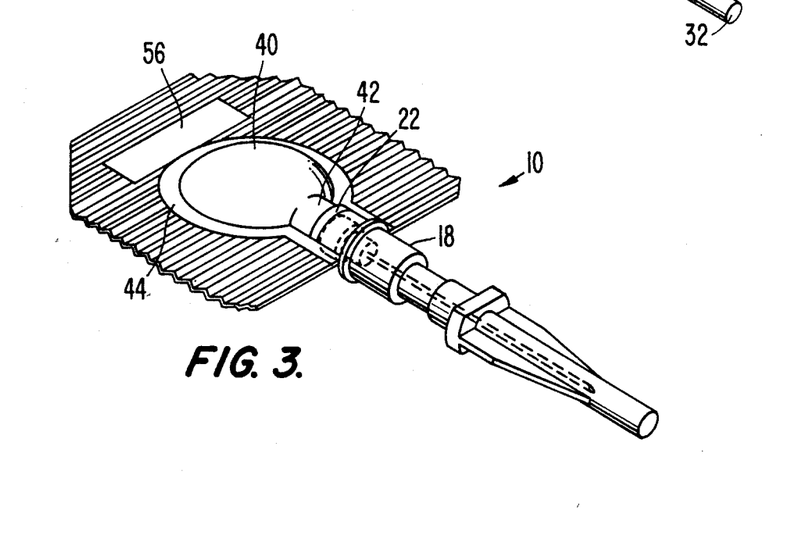
FIG. 3 is a diagram of an embodiment of the present invention.

As embodied in FIG. 2, the reservoir means is formed from a pair of sheets 38a and 38b of thermoplastic material. As shown in FIG. 3, each sheet 38 has a central portion 40, an injection neck portion 42, and a peripheral portion 44. Peripheral portion 44 is substantially flat, and injection neck portion 42 is expanded. Prior to administration of an injection to a patient, central portion 40 is expanded.

In accordance with the invention, the substantially flat peripheral portions of the two sheets of thermoplastic material are opposite and coextensive to each other and are sealed together face-to-face. The expanded central portions are opposite and coextensive to each other. The central and peripheral portions of the two sheets form a reservoir for storing the medicament.

Figure 5:
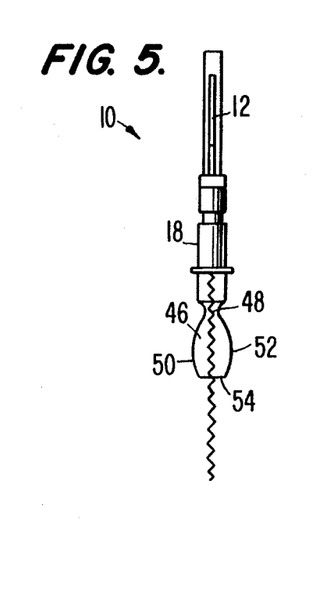
FIG. 5 is a diagram of a side view of an embodiment of the present invention prior to use.

A reservoir 46 is shown in FIGS. 2 and 5 prior to compression of central portions 40 of the pair of sheets 38 together. Reservoir 46 has sufficient volume to store an appropriate dose of the medicament being administered. As embodied herein, the shape of reservoir 46 is defined by the sealing together of the pair of sheets 38 at the peripheral portions and the separation of the two sheets at the central portions.

In the present invention, the expanded injection neck portions extend from the expanded central portions to a first end of each sheet, and are opposite and coextensive to each other. The expanded injection neck portions form an injection port extending from the reservoir and connected to the needle assembly means for directing the medicament from the reservoir to the needle assembly means.

Figure 4:
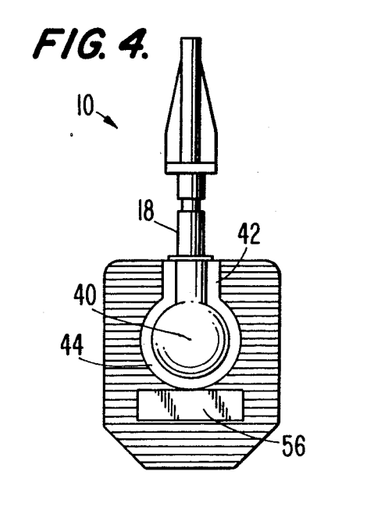
FIG. 4 is a diagram of a top view of an embodiment of the present invention.
Figure 6:
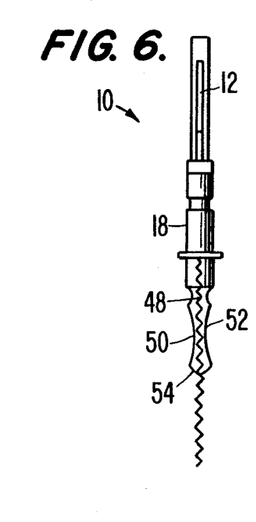
FIG. 6 is a diagram of a side view of an embodiment of the present invention rendered incapable of reuse.

In a preferred embodiment of the invention, injection port 48 is provided. As shown in FIGS. 2, 5, and 6, injection port 48 extends from reservoir 46 to the needle assembly means. The parts of expanded injection neck portions 42 of the two sheets which overlap nozzle 18 are sealed to the nozzle, as shown in FIGS. 3 and 4. Preferably, the injection port is connected to the needle assembly means by heat sealing, although an adhesive may be used if desired. The separation of the pair of sheets 38 at injection neck portions 42 provides a channel between the reservoir and the nozzle.

Needle hub 20 is positioned on needle 12 so that pointed end 14 is shorter than pointed end 16. The hypodermic needle and needle hub 20 are placed in nozzle 18 with shorter end 14 pointing at nozzle membrane 22. As shown in FIG. 2, large diameter first section 24 of needle hub 20 is pushed by open end 34 of protector cap 30 until the first section of the needle hub contacts nozzle membrane 22, which prevents end 14 of hypodermic needle 12 from being moved too far past the pierced nozzle membrane. In this position, nozzle membrane 22 is sufficiently thick relative to pointed end 14 of the hypodermic needle so that pointed end 14 pierces the nozzle membrane and just barely extends beyond the nozzle membrane toward reservoir 46.

Alternately, the side of nozzle membrane 22 facing reservoir 46 may be provided with an aperture (not shown) slightly larger in diameter than hypodermic needle 12 and extending partially through the nozzle membrane. In this alternate embodiment, after pushing needle hub 20 against the nozzle membrane, pointed end 14 extends into, but not significantly beyond, the aperture and penetrates the remainder of the nozzle membrane.

After needle hub 20 is laterally moved far enough within nozzle 18 to pierce nozzle membrane 22, the medicament stored in reservoir 46 can flow into the hypodermic needle and be injected into a patient. Since pointed end 14 of the hypodermic needle does not extend significantly beyond nozzle membrane 22, almost all of the medicament stored in reservoir 46 can be expelled into the hypodermic needle.

Two important features are provided in the syringe of the present invention. First, syringe 10 is not reusable after a single injection is administered to a patient. Second, in order to determine whether hypodermic needle 12 has been properly placed, it is possible to aspirate the needle, i.e., to draw material from a patient into syringe 10 prior to administering an injection to the patient. These functions are performed using reservoir 46.

It is important to recognize tha one of these functions, aspiration, is carried out when a reservoir is mostly full. In contrast, the other function, rendering a syringe unusable, is executed only after the reservoir has been emptied. Therefore, in accordance with the invention, reservoir 46 is designed to reform after partial compression in order to draw fluid into the reservoir, and to substantially collapse after complete compression to prevent the reservoir from being reformed.

In the present invention, the expanded central portions of the pair of sheets are compressible. Furthermore, in response to complete compression of both of the central portions together, the reservoir substantially collapses to prevent the reservoir from being reformed and to expel the medicament out of the reservoir. In the preferred embodiment shown in FIGS. 5 and 6, personnel administering an injection compress both central portions 40 of syringe 10 together. As a result, almost all of the medicament is forced out of reservoir 46 and into hypodermic needle 12 via injection port 48. After reservoir 46 collapses due to complete compression of the central portions together, as shown in FIG. 6, the reservoir cannot be reformed, preventing reuse of syringe 10.

In accordance with the invention, in response to partial compression of both of the central portions together, the reservoir partially collapses to expel some of the medicament out of the reservoir. Furthermore, the central portions, after partial compression of both of the central portions together and partial collapse of the reservoir, expand to reform the reservoir and to draw fluid into the reservoir, thereby aspirating the needle assembly means.

In a preferred embodiment of the invention, the syringe may be provided with reservoir means including a compressible convex first dome formed of a thermoplastic material and a compressible convex second dome formed of the thermoplastic material. As embodied in FIGS. 2 and 5, reservoir 46 is formed by a convex first dome 50 and a convex second dome 52. Preferably, each dome provides one hemisphere for the reservoir. The convex shape of domes 50 and 52 prior to compression permits storage of a medicament within reservoir 46.

Preferably, the reservoir means also includes a connecting member, coupled to the first and second domes, for spacing apart the first and second domes, to enable the reservoir means to substantially collapse in response to complete compression of both of the domes together. In response to complete compression of both of the domes together, each of the domes becomes concave and the reservoir means substantially collapses to prevent the reservoir means from being reformed.

In the preferred embodiment shown in FIGS. 2 and 5, a connecting member 54 is provided. In this embodiment, connecting member 54 is cylindrical in shape, is connected to the bottom of each of the hemispheres formed by the two domes, and spaces apart domes 50 and 52. As shown in FIG. 6, because of the presence of connecting member 54, personnel administering an injection must force both of the domes to assume a concave shape in order to completely compress domes 50 and 52 together. Once the domes are forced to assume a concave shape, reservoir 46 cannot be reformed and syringe 10 cannot be reused.

In accordance with this embodiment of the invention, in response to partial compression of both of the domes together, the reservoir means partially collapses. After partial compression of both of the domes together and partial collapse of the reservoir means, the domes expand to reform the reservoir means and to draw fluid into the reservoir, thereby aspirating the needle assembly means.

Unless connecting member 54 is placed between domes 50 and 52, the administration of an injection may not render the syringe unusable. Without the connecting member, the central portions of each sheet 38 are not forced past the bottom of the dome formed by that sheet. As a result, after complete compression of the domes together, it is possible for the central portions of each sheet to expand and for domes 50 and 52 to reassume a convex shape.

If a connecting member or its equivalent is not provided between the two domes that form a reservoir, a syringe has to be structured differently in order to prevent its reuse. For example, a reservoir may be designed so that one of the two domes is compressible, while the other dome is stationary. In such a structure, the reservoir collapses when the compressible dome is deformed into the stationary dome. However, in such a device, the two domes would be fabricated using different materials, or additional mechanical structure would be needed to prevent compression of the stationary dome. Therefore, in this example of an alternate structure, the resulting syringe is more expensive and more difficult to manufacture.

In the syringe of the present invention, a filling port means may be provided that extends from the reservoir means for filling the reservoir means with the medicament. Preferably, each of two thermoplastic sheets has an expanded filling neck portion, wherein the expanded filling neck portions extend from the expanded central portions to a second end of each sheet, and are opposite and coextensive to each other, to form a filling port extending from the reservoir.

In the preferred embodiment of the invention shown in FIG. 1, each sheet 38 has a filling neck portion 56 extending from central portion 40 to an end of the sheet. The filling neck portions are opposite and coextensive to each other, and are expanded prior to filling of reservoir 46 with a medicament. The separation of the pair of sheets 38 at filling neck portions 56 and the sealing together of the pair of sheets at surrounding peripheral portions 44 provides a channel into the reservoir from outside syringe 10. This channel constitutes a filling port 58 that is provided at the opposite end of syringe 10 from injection port 48. After the filling port is used to fill reservoir 46 with a medicament, filling neck portions 56 are sealed together so that the medicament can be stored.

In manufacturing syringe 10, any sheet may be used that is thermoplastic, is heat-sealable on at least one surface, and has the vapor impermeability required for the medicament being packaged. As embodied herein, these properties are achieved by coating a film of thermoplastic material with a material that has low water vapor transmissivity, and laminating together the film of thermoplastic material with a heat-sealable film. Preferably, polyethylene terepthalate is used as the thermoplastic substrate, the requisite vapor impermeability is provided by a coating of polyvinylidene chloride, and a low density polyethylene film is used to provide heat-sealable surfaces.

In the preferred embodiment of the invention, the thermoplastic material used to form the two sheets included in the reservoir means is made of a material that provides formability, rigidity, and strength. It also is desirable to use a material that can be radiation sterilized. Finally, there is a requirement that the materials used to manufacture the syringe be transparent so that the syringe can be inspected for the presence of particulate matter. Preferably, a film of polyethylene terephthalate that is about 120 microns thick is used as the thermoplastic material. This material is also referred to as PETG and is commercially available under the trademark KODAR.

In the preferred embodiment of the invention, the reservoir means includes a heat-sealable material, such as low density polyethylene. Preferably, the thermoplastic material and the heat-sealable material are laminated together using polyurethane as an adhesive, and the heat-sealable material is transparent. As a result, each sheet 3 is made up of at least two films of different materials.

In a preferred embodiment of the reservoir means, a material that has low water vapor transmissivity is included. These properties are designed to prevent water from passing through the material used to form reservoir 46. If a syringe is provided which allows water to escape from the reservoir, this may result in an unsafe dosage of the medicament that remains in the reservoir. Polyvinylidene chloride is a suitable material and is transparent. This material is also referred to as PVDC and is commercially available under the trademark SARAN. The material with low water vapor transmissivity is emulsion coated on a substrate of the thermoplastic material.

In summary, the process of manufacturing each sheet 38 begins with a polyethylene terephthalate film. An emulsion of polyvinylidene chloride is then coated on the film and dried. Finally, a low density polyethylene film is glued to the polyethylene terephthalate film using polyurethane.

The preferred method of manufacturing syringe 10 will now be described. To start the process, two separate rolls of material having thermoplastic and heat-sealable properties are provided to form the pair of sheets 38. The rolls contain enough material to mass produce a number of syringes 10.

The two rolls of material are unrolled together face-to-face. The material is unrolled so that the films of heat-sealable material on at least one surface of each sheet 38 are in contact with each other.

During the next step in the process, peripheral portion 44 in one sheet 38 is heat sealed to coextensive peripheral portion 44 in the other sheet, making use of the properties of the heat-sealable material in the films that are in contact with each other. As a result, the substantially flat peripheral portions of the two sheets are formed and are sealed together face-to-face. In another embodiment, an adhesive can be used to seal together the two sheets.

In accordance with the preferred embodiment of the invention, the substantially flat peripheral portions of the two sheets of thermoplastic material are sealed together face-to-face prior to formation of the expanded portions of the two sheets. The central portions, injection neck portions, and filling neck portions of the two sheets are expanded to form the reservoir, injection port, and filling port after the peripheral portions are sealed together by injecting compressed gas between the unsealed portions of the two sheets until these portions expand to fill the cavities of a mold. Alternately, these portions of the two sheets are expanded to form the reservoir, injection port, and filling port after the peripheral portions are sealed together by drawing apart the unsealed portions of the two sheets using a vacuum until these unsealed portions expand to fill the cavities of the mold.

Preferably, a mold (die) is provided so that the reservoir and port means may be formed. In the mold (not shown), cavities are provided to define the desired shape of reservoir 46, injection port 48, and filling port 58.

To manufacture the preferred embodiment of syringe 10, the mold has a pair of cavities, each of which is dome-shaped at the bottom and cylindrical at the top. The pair of cavities of the mold and central portions 40 of the two sheets are coextensive with each other. As a result, a syringe with two convex domes 50 and 52 and connecting member 54 can be fabricated. The mold is heated so that the thermoplastic material included in the pair of sheets 38 is softened and can be thermoformed. Compressed air is then injected (blown) between the central portions 40 of the two sheets to separate and expand the central portions. The compressed air forces the central portions to fill the cavities in the mold and assume the appropriate shape of the reservoir. Alternately, reservoir 46 can be formed using a vacuum to draw apart central portions 40. Alternately, it also may be possible to fabricate the reservoir using a mechanical plug (not shown).

The remaining portions of each sheet 38, i.e., injection neck portions 42 and filling neck portions 56, also may be thermoformed at the same time using compressed gas or a vacuum to expand those portions of the sheets. Separate cavities coextensive with the injection neck portions and the filling neck portions of the pair of sheets 38 must be provided in the mold to define the shape of the injection port and the filling port of syringe 10. In this way, injection port 48, filling port 58, and reservoir 46 can be formed together.

· When syringe 10 is fabricated by using compressed gas or a vacuum to form reservoir 46 after heat sealing of the peripheral portions surrounding the reservoir, important advantages are obtained. In syringe 10, an excellent seal is first provided, and then the reservoir is blown or drawn open. As a result, the integrity of reservoir 46 is secured using a convenient and economical process, and rupture of syringe 10 at the sealing areas is less likely.

In other devices, a reservoir formed of two or more sheets is generally formed by sealing together the parts of the reservoir after these parts have assumed their desired shapes. In these devices, failures of the seal due to delamination of the sheets or other reasons are more likely. Furthermore, manufacture of such devices may be more difficult and expensive because the tolerances are made tighter during heat sealing to ensure the integrity of the seals between the parts of the reservoir.

After the reservoir for syringe 10 is formed, the next step in the process is coupling of the needle assembly means to the injection port. Preferably, nozzle 18 is used to provide the needle assembly means with a tube for holding hypodermic needle 12 and needle hub 20, and the nozzle and the injection port are cylindrical in shape. The diameters of nozzle 18 and injection port 48 are selected so that the nozzle can be inserted within the injection port.

Next, the needle assembly means is heat sealed to the injection port. In the preferred embodiment of syringe 10, nozzle 18 also is formed of a heat sealable material, such as low density polyethylene. Since nozzle 18 is inserted within injection port 48, the films of heat-sealable material on at least one surface of each sheet 38 will be in contact with nozzle 18.

These steps are repeated using the rest of the material in the two rolls to mass produce a number of syringes 10 at relatively low cost. As a result, reels of about 1000 syringes are obtained, which can then be sterilized. Preferably, radiation is used as the most cost effective way to sterilize the syringes.

After these steps are performed, the only remaining step is filling of reservoir 46 with an appropriate medicament. This step is usually performed separately from the other steps in the process. Reservoir 46 is filled with the medicament using filling port 58. During the filling operation, which is performed in a sterile environment, most of the air in the reservoir is vented and displaced by the medicament. Following the filling step, filling neck portions 56 of the two sheets 38 are heat sealed together.

When syringe 10 is used to administer an injection, it is important to point the syringe downward so that reservoir 46 is on top and hypodermic needle 12 is on bottom. In this way, personnel using the syringe can prevent any air left in reservoir 46 from being injected into a patient.

There are a number of vaccines and medicines that are administered using a syringe. Syringe 10 can be used to deliver for intravenous or intramuscular injection such medicaments as hepatitis B vaccine, tetanus toxoid vaccine, heparin, atropine sulfate, morphine sulfate, ranitidine, lidocaine, meperidine, naloxone, furosemide, and dexamethasone sodium phosphate.

Syringe 10 also is capable of use with a lyophilized material requiring reconstitution of the medicament by adding a diluent to the material. In the case of such a lyophilized material, the reservoir means may be structured to contain two adjacent compartments separated by a seal. A drug or vaccine can be reconstituted by rupturing the seal between a first compartment containing water and a second compartment containing the lyophilized material. Alternately, a port can be provided so that sterile water can be added to the reservoir at the appropriate time. In such an embodiment, it is not necessary to include a material with low water vapor transmissivity in the reservoir.

It will be apparent to those skilled in the art that various modifications and variations can be made in the structure or method of manufacture of the syringe of the present invention without departing from the scope or spirit of the invention. For example, the needle assembly means can be structured in a variety of ways. Thus, it is intended that the present invention cover modifications and variations of this invention, provided they come within the scope of the appended claims and their equivalents.

What is claimed is:

1. A single-use disposable syringe for providing a medicament for injection into a patient, the syringe comprising:

needle assembly means for injecting the medicament into the patient; and reservoir means for storing the medicament and for expelling the medicament into the needle assembly means, the reservoir means including two sheets of thermoplastic material, wherein each of the two thermoplastic sheets is comprised of an expanded central portion, an expanded injection neck portion, an expanded filling neck portion, and a substantially flat peripheral portion, in which the substantially flat peripheral portions of the two sheets of thermoplastic material are opposite and coextensive to each other and are sealed together face-to-face, and the expanded central portions are opposite and coextensive to each other, to form a reservoir for storing the medicament, in which the expanded injection neck portions extend from the expanded central portions to a first end of each sheet, and are opposite and coextensive to each other, to form an injection port extending from the reservoir and connected to the needle assembly means for directing the medicament from the reservoir to the needle assembly means, and in which the expanded filling neck portions extend from the expanded central portions to a second end of each sheet, and are opposite and coextensive to each other, to form a filling port extending from the reservoir for filling the reservoir with the medicament;

wherein the expanded central portions are compressible, and in response to complete compression of both of the central portions together, the reservoir substantially collapses to prevent the reservoir from being reformed and to expel the medicament out of the reservoir;

wherein in response to partial compression of both of the central portions together, the reservoir partially collapses to expel some of the medicament out of the reservoir; and wherein the central portions, after partial compression of both of the central portions together and partial collapse of the reservoir, expand to reform the reservoir and to draw fluid into the reservoir, thereby aspirating the needle assembly means.

2. A single-use disposable syringe in accordance with claim 1, in which the needle assembly means includes:

a hypodermic needle pointed at both ends;

hub means fastened to the hypodermic needle for supporting the hypodermic needle;

a tube for holding the hypodermic needle and the hub means, having a closed end connected to the injection port and an open end;

means for laterally moving the hypodermic needle within the tube to pierce the closed end of the tube with one of the pointed ends of the hypodermic needle; and means for protecting the hypodermic needle.

3. A single-use disposable syringe in accordance with claim 1, in which the thermoplastic material is comprised of polyethylene terephthalate.

4. A injection device in accordance with claim 1, in which the sheets of thermoplastic material include a heat-sealable material at least on the sides of the thermoplastic sheets that face each other.

5. A single-use disposable syringe in accordance with claim 4, in which the heat-sealable material is comprised of low density polyethylene.

6. A single-use disposable syringe in accordance with claim 4, in which the reservoir means includes a material that has low water vapor transmissivity.

7. A single-use disposable syringe in accordance with claim 6, in which the material that has low water vapor transmissivity is comprised of polyvinylidene chloride.

8. A single-use disposable syringe in accordance with claim 1, in which the expanded central portions form a reservoir comprising:
   a compressible convex first dome;
   a compressible convex second dome; and
   a connecting member, coupled to the first and second domes, for spacing apart the first and second domes, to enable the reservoir to substantially collapse in response to complete compression of both of the domes together;
   wherein in response to complete compression of both of the domes together, each of the domes becomes concave to prevent the reservoir from being reformed.

9. A single-use disposable syringe in accordance with claim 8, in which the connecting member forms a cylinder.

10. A single-use disposable syringe for providing a medicament for injection into a patient, the syringe comprising:
    needle assembly means for injecting the medicament into the patient;
    reservoir means for storing the medicament and for expelling the medicament into the needle assembly means, the reservoir means including
    a compressible convex first dome formed of a thermoplastic material;
    a compressible convex second dome formed of the thermoplastic material; and
    a connecting member, coupled to the first and second domes, for spacing apart the first and second domes, to enable the reservoir means to substantially collapse in response to complete compression of both of the domes together;
    wherein in response to complete compression of both of the domes together, each of the domes becomes concave to prevent the reservoir means from being reformed; and
    injection port means extending from the reservoir means and connected to the needle assembly means for directing the medicament from the reservoir means to the needle assembly means;
    wherein the reservoir means substantially collapses in response to complete compression of both of the domes together to prevent the reservoir means from being reformed and to expel the medicament out of the reservoir means;
    wherein in response to partial compression of both of the domes together, the reservoir means partially collapses to expel some of the medicament out of the reservoir means; and
    wherein the domes, after partial compression of both of the domes together and partial collapse of the reservoir means, expand to reform the reservoir means and to draw fluid into the reservoir means, thereby aspirating the needle assembly means.

11. A single-use disposable syringe in accordance with claim 10, further comprising filling port means extending from the reservoir means for filling the reservoir means with the medicament.

12. A single-use disposable syringe in accordance with claim 10, in which the needle assembly means includes:
    a hypodermic needle pointed at both ends;
    hub means fastened to the hypodermic needle for supporting the hypodermic needle;
    a tube for holding the hypodermic needle and the hub means, having a closed end connected to the injection port and an open end;
    means for laterally moving the hypodermic needle within the tube to pierce the closed end of the tube with one of the pointed ends of the hypodermic needle; and
    means for protecting the hypodermic needle.

13. A single-use disposable syringe in accordance with claim 10, in which the thermoplastic material is comprised of polyethylene terephthalate.

14. A injection device in accordance with claim 10, in which the thermoplastic material includes a heat-sealable material at least on the sides of the thermoplastic material that face each other.

15. A single-use disposable syringe in accordance with claim 14, in which the heat-sealable material is comprised of low density polyethylene.

16. A single-use disposable syringe in accordance with claim 14, in which the reservoir means includes a material that has low water vapor transmissivity.

17. A single-use disposable syringe in accordance with claim 16, in which the material that has low water vapor transmissivity is comprised of polyvinylidene chloride.

18. A single-use disposable syringe for providing a medicament for injection into a patient, the syringe comprising:
    needle assembly means for injecting the medicament into the patient; and
    reservoir means for storing the medicament and for expelling the medicament into the needle assembly means, the reservoir means including two sheets of thermoplastic material, wherein each of the two thermoplastic sheets is comprised of an expanded central portion, an expanded injection neck portion, an expanded filling neck portion, and a substantially flat peripheral portion,
    in which the substantially flat peripheral portions of the two sheets of thermoplastic material are opposite and coextensive to each other and are sealed together face-to-face, and the expanded central portions are opposite and coextensive to each other, to form a reservoir for storing the medicament,
    in which the expanded injection neck portions extend from the expanded central portions to a first end of each sheet, and are opposite and coextensive to each other, to form an injection port extending from the reservoir and connected to the needle assembly means for directing the medicament from the reservoir to the needle assembly means, in which the expanded filling neck portions extend from the expanded central portions to a second end of each sheet, and are opposite and coextensive to each other, to form a filling port extending from the reservoir for filling the reservoir with the medicament, and in which the substantially flat peripheral portions of the two sheets of thermoplastic material are sealed together face-to-face prior to formation of the expanded central portions of the two sheets, and the central portions of the two sheets are expanded to form the reservoir after the peripheral portions are sealed together by injecting compressed gas between the central portions of the two sheets until the central portions expand to fill a cavity of a mold;

wherein the expanded central portions are compressible, and in response to complete compression of both of the central portions together, the reservoir substantially collapses to prevent the reservoir from being reformed and to expel the medicament out of the reservoir;

wherein in response to partial compression of both of the central portions together, the reservoir partially collapses to expel some of the medicament out of the reservoir; and wherein the central portions, after partial compression of both of the central portions together and partial collapse of the reservoir, expand to reform the reservoir and to draw fluid into the reservoir, thereby aspirating the needle assembly means.

19. A single-use disposable syringe in accordance with claim 18, in which the expanded central portions form a reservoir comprising:

a compressible convex first dome;
a compressible convex second dome; and
a connecting member, coupled to the first and second domes, for spacing apart the first and second domes, to enable the reservoir to substantially collapse in response to complete compression of both of the domes together;

wherein in response to complete compression of both of the domes together, each of the domes becomes concave to prevent the reservoir from being reformed.

20. A single-use disposable syringe for providing a medicament for injection into a patient, the syringe comprising:

needle assembly means for injecting the medicament into the patient; and reservoir means for storing the medicament and for expelling the medicament into the needle assembly means, the reservoir means including two sheets of thermoplastic material, wherein each of the two thermoplastic sheets is comprised of an expanded central portion, an expanded injection neck portion, an expanded filling neck portion, and a substantially flat peripheral portion, in which the substantially flat peripheral portions of the two sheets of thermoplastic material are opposite and coextensive to each other and are sealed together face-to-face, and the expanded central portions are opposite and coextensive to each other, to form a reservoir for storing the medicament, in which the expanded injection neck portions extend from the expanded central portions to a first end of each sheet, and are opposite and coextensive to each other, to form an injection port extending from the reservoir and connected to the needle assembly means for directing the medicament from the reservoir to the needle assembly means, in which the expanded filling neck portions extend from the expanded central portions to a second end of each sheet, and are opposite and coextensive to each other, to form a filling port extending from the reservoir for filling the reservoir with the medicament, and in which the substantially flat peripheral portions of the two sheets of thermoplastic material are sealed together face-to-face prior to formation of the expanded central portions of the two sheets, and the central portions of the two sheets are expanded to form the reservoir after the peripheral portions are sealed together by drawing apart the central portions of the two sheets using a vacuum until the central portions expand to fill a cavity of a mold;

wherein the expanded central portions are compressible, and in response to complete compression of both of the central portions together, the reservoir substantially collapses to prevent the reservoir from being reformed and to expel the medicament out of the reservoir;

wherein in response to partial compression of both of the central portions together, the reservoir partially collapses to expel some of the medicament out of the reservoir; and wherein the central portions, after partial compression of both of the central portions together and partial collapse of the reservoir, expand to reform the reservoir and to draw fluid into the reservoir, thereby aspirating the needle assembly means.

21. A single-use disposable syringe in accordance with claim 20, in which the expanded central portions form a reservoir comprising:

a compressible convex first dome;
a compressible convex second dome; and
a connecting member, coupled to the first and second domes, for spacing apart the first and second domes, to enable the reservoir to substantially collapse in response to complete compression of both of the domes together;

wherein in response to complete compression of both of the domes together, each of the domes becomes concave to prevent the reservoir from being reformed.

22. A single-use disposable syringe for providing an injection into a patient, the syringe comprising:

a medicament;
needle assembly means for injecting the medicament into the patient; and reservoir means for storing the medicament and for expelling the medicament into the needle assembly means, the reservoir means including two sheets of thermoplastic material, wherein each of the two thermoplastic sheets is comprised of an expanded central portion, an expanded injection neck portion, and a substantially flat peripheral portion, in which the substantially flat peripheral portions of the two sheets of thermoplastic material are opposite and coextensive to each other and are sealed together face-to-face, and the expanded central portions are opposite and coextensive to each other, to form a reservoir for storing the medicament, and in which the expanded injection neck portions extend from the expanded central portions to a first end of each sheet, and are opposite and coextensive to each other, to form an injection port extending from the reservoir and connected to the needle assembly means for directing the medicament from the reservoir to the needle assembly means;

wherein the expanded central portions are compressible, and in response to complete compression of both of the central portions together, the reservoir substantially collapses to prevent the reservoir from being reformed and to expel the medicament out of the reservoir;

wherein in response to partial compression of both of the central portions together, the reservoir partially collapses to expel some of the medicament out of the reservoir; and wherein the central portions, after partial compression of both of the central portions together and partial collapse of the reservoir, expand to reform the reservoir and to draw fluid into the reservoir, thereby aspirating the needle assembly means.

23. A single-use disposable syringe in accordance with claim 22, in which the needle assembly means includes:

a hypodermic needle pointed at both ends;

hub means fastened to the hypodermic needle for supporting the hypodermic needle;

a tube for holding the hypodermic needle and the hub means, having a closed end connected to the injection port and an open end;

means for laterally moving the hypodermic needle within the tube to pierce the closed end of the tube with one of the pointed ends of the hypodermic needle; and means for protecting the hypodermic needle.

24. A single-use disposable syringe in accordance with claim 22, in which the expanded central portions form a reservoir comprising:

a compressible convex first dome;

a compressible convex second dome; and a connecting member, coupled to the first and second domes, for spacing apart the first and second domes, to enable the reservoir to substantially collapse in response to complete compression of both of the domes together;

wherein in response to complete compression of both of the domes together, each of the domes becomes concave to prevent the reservoir from being reformed.

* * * * *